United States Patent

Clemence et al.

Patent Number: 5,254,566
Date of Patent: Oct. 19, 1993

[54] DECAHYDROQUINOLINE COMPOUNDS

[75] Inventors: Francois Clemence, Paris; Gilles Hamon, Le Raincy; Odile Le Martret, Paris, all of France

[73] Assignee: Roussel Uclaf, France

[21] Appl. No.: 950,087

[22] Filed: Sep. 22, 1992

[30] Foreign Application Priority Data

Sep. 24, 1991 [FR] France .................. 91 11736

[51] Int. Cl.$^5$ .................. A61K 31/44; C07D 401/04
[52] U.S. Cl. .................. 514/313; 546/159; 544/128; 544/363; 514/255; 514/235.2
[58] Field of Search .................. 546/159; 514/313, 255, 514/235.2; 544/128, 363

[56] References Cited

U.S. PATENT DOCUMENTS 2,050,971  8/1936  Jensch .................. 546/159

Primary Examiner—C. Warren Ivy
Assistant Examiner—Zinna N. Davis
Attorney, Agent, or Firm—Bierman and Muserlian

[57] ABSTRACT

A compound selected from the group consisting of racemates, enantiomeric and diastereoisomeric forms of a compound of the formula

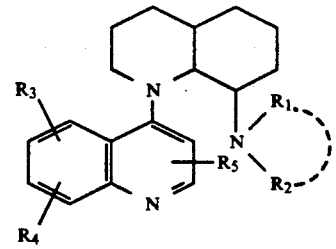

wherein $R_1$ and $R_2$ are individually selected from the group consisting of hydrogen and alkyl of 1 to 5 carbon atoms optionally substituted with at least one halogen, hydroxy, alkyl or alkoxy of 1 to 4 carbon atoms or taken together with the nitrogen to which they are attached form a heterocycle optionally containing a heteroatom selected from the group consisting of —O—, —S— and nitrogen optionally substituted with alkyl or alkoxy of 1 to 5 carbon atoms, optionally substituted benzyl and phenyl, $R_3$ and $R_4$ are individually selected from the group consisting of hydrogen, halogen, hydroxy and alkyl and alkoxy of 1 to 5 carbon atoms optionally substituted with at least one substituent selected from the group consisting of halogen, hydroxy, phenyl and alkyl and alkoxy of 1 to 4 carbon atoms, $R_5$ is hydrogen or alkyl of 1 to 5 carbon atoms optionally substituted with at least one member of the group consisting of halogen, hydroxy, phenyl and alkyl and alkoxy of 1 to 4 carbon atoms and its non-toxic, pharmaceutically acceptable acid addition salts and quaternary ammonium salts having analgesic activity and their preparation.

9 Claims, No Drawings

DECAHYDROQUINOLINE COMPOUNDS

STATE OF THE ART

Related prior art includes U.S. Pat. No. 2,359,329 and French Patent No. 1,510,009 and No. M 3,657.

OBJECTS OF THE INVENTION

It is an object of the invention to provide the novel compounds of formula I and their acid addition and quaternary ammonium salts and a process for their preparation.

It is another object of the invention to provide novel analgesic compositions and a method of relieving pain in warm-blooded animals.

These and other objects and advantages will become obvious from the following detailed description.

THE INVENTION

The novel compounds of the invention are selected from the group consisting of racemates, enantiomeric and diastereoisomeric forms of a compound of the formula

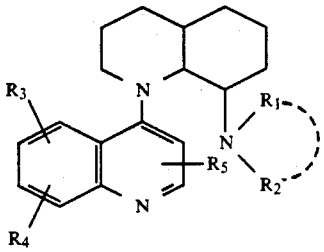

I wherein $R_1$ and $R_2$ are individually selected from the group consisting of hydrogen and alkyl of 1 to 5 carbon atom optionally substituted with at least one halogen, hydroxy, alkyl or alkoxy of 1 to 4 carbon atoms or taken together with the nitrogen to which they are attached form a heterocycle optionally containing a heteroatom selected from the group consisting of —O—, —S— and nitrogen optionally substituted with alkyl or alkoxy of 1 to 5 carbon atoms, optionally substituted benzyl and phenyl, $R_3$ and $R_4$ are individually selected from the group consisting of hydrogen, halogen, hydroxy and alkyl and alkoxy of 1 to 5 carbon atoms optionally substituted with at least one substituent selected from the group consisting of halogen, hydroxy, phenyl and alkyl and alkoxy of 1 to 4 carbon atoms, $R_5$ is hydrogen or alkyl of 1 to 5 carbon atoms optionally substituted with at least one member of the group consisting of halogen, hydroxy, phenyl and alkyl and alkoxy of 1 to 4 carbon atoms and its non-toxic, pharmaceutically acceptable acid addition salts and quaternary ammonium salts.

Examples of alkyl and alkoxy in the compounds of formula I are methyl, ethyl, n-propyl, isopropyl, butyl, isobutyl, sec.-butyl, tert.-butyl, n-pentyl, methoxy, ethoxy, isopropoxy, n-propoxy, n-butoxy, tert.-butyl and sec.-butoxy. Halogen is preferably chlorine but may also be fluorine, bromine or iodine.

Examples of

are monoalkyl- or dialkylamino with linear or branched alkyl of 1 to 5 carbon atoms such as methyl, ethyl, isopropyl, n-butyl or isobutyl and specifically methylamino, dimethylamino, ethylamino, ethylmethylamino, isopropylamino, isopropylmethylamino and diisopropylamino.

When $R_1$ and $R_2$ form together with the nitrogen atom to which they are attached a heterocycle, it is, for example, pyrrolidinyl, piperidinyl, morpholinyl or piperazinyl optionally substituted as indicated above. The heterocycle that $R_1$ and $R_2$ can form with the nitrogen atom to which they are attached can be substituted, preferably by one or more substituents selected from linear or branched alkyl and alkoxy of 1 to 5 carbon atoms, phenyl and benzyl, all optionally substituted as indicated above.

When the alkyl is substituted, for example, trifluoromethyl and hydroxymethyl can be mentioned. As examples of such substituted radicals formed by $R_1$ and $R_2$ with the nitrogen atom to which they are linked there can be mentioned, methylpiperazinyl, ethylpiperazinyl, propylpiperazinyl, phenylpiperazinyl, chlorophenylpiperazinyl, trifluoromethylphenylpiperazinyl and benzylpiperazinyl.

Among the preferred compounds of formula I are those wherein $R_3$ is hydrogen, $R_4$ is 7-chloro or 8-$CF_3$ and $R_5$ is hydrogen and those wherein $R_3$ is hydrogen, $R_4$ is 7-chloro or 8-trifluoromethyl and $R_5$ is 1-$CF_3$.

The non-toxic, pharmaceutically acceptable acid addition salts may be made with inorganic acids such as hydrochloric acid, hydrobromic acid, hydroiodic acid, nitric acid, sulfuric acid and phosphoric acid or organic acids such as propionic acid, acetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids such as methanesulfonic acid, ethanesulfonic acid, propanesulfonic acid, alkyl-disulfonic acids such as methanedisulfonic acid, $\alpha$, $\beta$-ethanedisulfonic acid, arylmonosulfonic acids such as benzenesulfonic acid and aryldisulfonic acids.

More particularly, the preferred products of formula I are those in which $R_1$ and $R_2$ form together with the nitrogen to which they are attached pyrrolidinyl, $R_3$, $R_4$ and $R_5$ are individually hydrogen, halogen or trifluoromethyl, the said products of formula I being able to be in all possible racemic, enantiomeric and diastereoisomeric isomer forms and in the form of addition salts with acids or quaternary ammonium salts of said products of formula I.

Particularly preferred are (4a $\alpha$, 8$\alpha$, 8a $\alpha$) ($\pm$) 1-(7-chloro-4-quinolinyl)-decahydro-8-(1-pyrrolidinyl) quinoline and (4a $\alpha$, 8$\alpha$, 8a $\alpha$) ($\pm$) 1-(7-chloro-4-quinolinyl)-decahydro-8-(1-pyrrolidinyl) quinoline dihydrochloride and their addition salts with acids or their quaternary ammonium salts.

The novel process of the invention for the preparation of compounds of formula I comprises reacting a compound of the formula

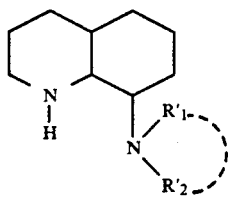

II in which R′₁ and R′₂ have the definitions for R₁ and R₂ in which the optional reactive functions are optionally protected, or one or both of R′₁ and R′₂ is a protector group of amino or monoalkylamino with a compound of the formula

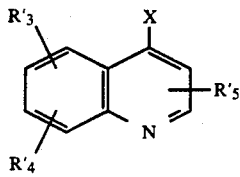

III in which R′₃, R′₄ and R′₅ have the definitions of R₃, R₄ and R₅ respectively in which the optional reactive functions are optionally protected and X is halogen or a parting group to obtain a compound of the formula

IV

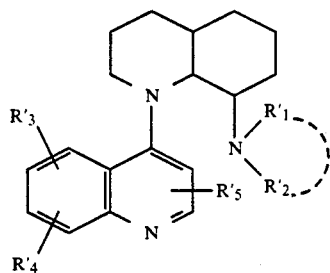

in which R′₁, R′₂, R′₃, R′₄ and R′₅ have the above definitions, subjecting the latter, if necessary and if desired, to one or more of the following reactions, in any order:

an elimination reaction of the protective groups that can be carried by the protected reactive functions, a salification reaction with an acid to obtain the corresponding salt, a resolution reaction of racemic forms into resolved products, the said products of formula I thus obtained being in all possible racemic, enantiomeric and diastereoisomeric isomer forms, and in the form of addition salts with mineral or organic acids or quaternary ammonium salts of said products of formula I.

Under the preferred conditions of the process, the above reaction is carried out by heating at reflux the products of formulae II and III in a solvent such as dimethylformamide or dimethylformamide with sodium carbonate or ethoxyethanol in the presence of sodium bicarbonate, the reaction being preferably carried out in the presence of copper sulfate.

In the products of formula III, X can be halogen such as chlorine or bromine and preferably chlorine or can be a parting group such as mesyl or tosyl.

The products of formula I can be represented by the products of formula IV or be obtained by elimination of the protective groups of the reactive functions that can be carried by these products of formula IV.

The various reactive functions that can, if necessary, be protected in an appropriate manner, are for example, hydroxyls carried by R₁, R₂, R₃, R₄ and R₅ or by R₃ and R₄; amino and monoalkylamino that can be represented by

The following non-exhaustive list of examples of the protection of reactive functions can be mentioned: hydroxyls can be protected for example by trimethylsilyl, dihydropyran, benzyl, methoxy or methoxymethyl and amino groups can be protected for example by trityl, benzyl, tert.-butoxycarbonyl, phthalimido or others known in the chemistry of the peptides.

The elimination of these protective groups is carried out under standard conditions known to one skilled in the art, notably acid hydrolysis carried out with an acid such as hydrochloric acid, benzene sulfonic acid or p-toluene sulfonic acid, formic acid or trifluoroacetic acid.

The phthalimido group is eliminated by hydrazine. A list of different protective groups which can be used will be found for example in the Patent No. BF 2,499,995.

The products described above can, if desired, be the object of a salification reaction to give acid addition salts or quaternary ammonium salts for example by the usual methods known to a man skilled in the art.

The optically active forms of the products of formula I can be prepared by resolution of the racemates by the usual methods.

The analgesic compositions of the invention are comprised of an analgesically effective amount of at least one compound of formula I and its non-toxic, pharmaceutically acceptable acid addition or quaternary ammonium salts and an inert pharmaceutical carrier. The compositions may be in the form of tablets, dragees, capsules, granules, suppositories, creams, ointments, gels, injectable solutions or suspensions and aerosols.

Examples of pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have in particular, a strong affinity for the opiate receptors and especially for the kappa receptors and are endowed with central analgesic properties as well as diuretic properties and some of them have anti-arythmic, anti-ischemic and hypotensive properties. The compositions also have anti-parasitic and particularly anti-paludal properties.

The compositions are useful for the relief of pain of whatever origin, for example a pain of a muscular, articular or nervous nature and are useful in the treatment of toothaches, migraines, shingles, in the treatment of intense pains, particularly those resistant to peripheral antalgesics, for example during the neoplasia process, in the treatment of pancreatitis, nephretic or biliary colics, in the treatment of post-operative and post-traumatic pains. They can also be used in the treatment of cerebral insufficiency of ischemic origin, in disorders of the memory and attention and particularly in the treatment of malaria. They can also be used in the treatment of oedematous syndromes, cardiac insufficiency, certain obesities, cirrhoses, in the treatment of severe and refractory oedemas, in particular those of congestive cardiac insufficiency and in the long-term treatment of arterial hypertension.

The method of the invention for relieving pain in warm-blooded animals, including humans, comprises administering to warm-blooded animals an analgesically effective amount of at least one compound of formula I or its non-toxic, pharmaceutically acceptable acid addition or quaternary ammonium salts. The compounds may be administered orally, rectally, parenterally or topically to the skin and mucous membranes. The usual active dose is 0.66 to 13.33 mg/kg depending on the condition treated, the specific compound and method of administration.

The starting compounds of formula II may be prepared by known techniques such as in French patent No. 2,592,879. The compounds of formula III such as 4,7-dichloroquinoline are commerically available and may be made by the procedures of German patent No. 2,806,909 or French patent No. 1,584,746.

In the following examples, there are described several preferred embodiments to illustrate the invention. However, it should be understood that the invention is not intended to be limited to the specific embodiments.

EXAMPLE 1

(4aα, 8α, 8aα) (±) 1-(7-chloro-4-quinolinyl)-decahydro-8-(1-pyrrolidinyl)-quinoline 7.13 g of 4,7-dichloroquinoline and 6.25 g of [4a(RS) (4aα, 8α, 8a α) (±)] decahydro-8-(1-pyrrolidinyl) quinoline (obtained by French patent No. 2,592,879) were introduced at 20° C. into 30 ml of dimethylformamide in the presence of 206 mg of anhydrous copper sulfate. The solution was refluxed with stirring for approximately 2 hours. After distillation under reduced pressure, the mixture was cooled to ambient temperature and diluted with 100 ml of water, then alkalinized to approximately a pH of 10 with sodium carbonate. After separating and rinsing three times with 50 ml of water, the insoluble part was taken up in 100 ml of methylene chloride, followed by washing with 100 ml of water, drying, filtering, rinsing and distilling under reduced pressure. The dry extract was taken up in 80 ml of ethyl ether at ambient temperature, filtered and dried under reduced pressure. The dry extract was impasted in 10 ml of isopropyl ether, separated, rinsed with isopropyl ether and dried under vacuum at approximately 50° C. to obtain 1.66 g of the expected product in the form of the base melting at 136° C. to 138° C.

EXAMPLE 2

(4a α, 8α, 8aα) (±) 1-(7-chloro-4-quinolinyl)-decahydro-8-(1-pyrrolidinyl)-quinoline dihydrochloride 1.66 g of the product of Example 1 were dissolved in 8 ml of hot isopropanol. The solution was filtered and rinsed with 7 ml of isopropanol. 2 ml of a solution of hydrogen chloride in ethanol (approximately 6.6N) were added and crystallization was started. Separation took place at ambient temperature, followed by rinsing three times with 2 ml of isopropanol and three times with 5 ml of ethyl ether and after crystallization from 30 ml of isopropanol with 1.5% of water and then from 7 ml of ethanol 100, the crystals were dried at ambient temperature to obtain 1.3 g of the expected product melting at 220° C.

| NMR IN CDCl$_3$ | |
|---|---|
| 3.78 (m) | C$_6$H$_5$-N-CH 1H |
| 8.53 (d) | H in position 2 on quinoline |
| 6.75 (d) | H in position 3 on quinoline |
| 7.32 (dd) | H in position 6 on quinoline |
| 7.88 (dd) | H in position 5 on quinoline |
| 0.8 to 3.4 | the other protons |

EXAMPLE 3

Tablets were prepared containing 200 mg of the product of Example 2 and sufficient excipient of lactose, talc, starch and magnesium stearate for a tablet of 800 mg.

EXAMPLE 4

An injectable solute (intra-muscular route) was prepared containing 50 mg of the product of Example 2 and sterile solvent in sufficient quantity for 10 ml.

Pharmacological Study

1) Bonding to the kappa opiate receptor in vitro

Membrane residues were used, kept at −30° C. for about 30 days and prepared from guinea-pigs' brains. These residues were suspended in a Tris pH 7.7 buffer and 2 ml fractions were divided into hemolysis tubes. 1 nM of 9$^3$H Ethylketocyclazocine and the product under test were added. The product was first tested at $5 \times 10^{-6}$M (three times). When the product tested displaced more than 50% of the radioactivity linked specifically to the receptor, it was tested again in a range of 7 concentrations to determine the dose which inhibited 50% of the radioactivity linked specifically to the receptor. Thus, the 50% inhibiting concentration was determined.

The non-specific bonding was determined by the addition of a product known under the name U-50488 H at $10^{-5}$M (three times). After incubation at 25° C. for 40 minutes, the suspension was put in a water bath at 0° C. for 5 minutes, then filtered under reduced pressure, rinsed with a Tris pH 7.7 buffer and the radioactivity was counted in the presence of scintillating Triton (R).

The results were expressed directly as a 50% inhibiting concentration, IC$_{50}$, (that is to say as the concentration of product studied, expressed in nM, necessary to displace 50% of the specific radioactivity fixed to the receptor studied).

| Product of Example | IC$_{50}$ in nM |
|---|---|
| 2 | 30,600 |

2) Test for determining the anti-paludal activity in vitro

The culturing of Plasmodium falciparum "in vitro" was carried out in cupulas on polystyrene plates used for tissue culture. It was carried out at 37° C. in a CO$_2$ oven by the technique of TRAGER et al (1976–1978) on a modified RPMI 1640 medium (AZOULAY et al 1983) buffered with a mixture of HEPES buffer (40 m.moles/l), glucose (4 g/l) and 10 percent human serum. The anti-malarial activity "in vitro" of the different products tested was studied on two different strains of Plasmodium falciparum, namely an FCC2 strain sensitive to chloroquine and an FZ strain resistant to chloroquine (R3 type resistance).

Measurement of the inhibition of proliferation in continuous culture (Trager-Polonsky 1981)

This test permited measurement of the action of the product to be tested on the maturation of the trophozoite into the schizont, but also the possibility of repenetration of the merozoites, released by the breaking up of the malarial rosettes, in healthy red corpuscles, and their conversion into trophozoites. The strains of Plasmodium falciparum used carry out a complete cycle in 48 hours.

The RPS medium containing 40 mM of H.E.P.E.S. buffer and enriched with 2 g of glucose permitted a good development of the culture without renewing the medium for two days. The parasitized red blood corpuscles were suspended in the RPS 10 medium containing the product to be tested at the chosen concentration.

The starting parasitemia was between 0.2 and 0.3%.

0.7 ml of the globular suspension was deposited in each cupula and each concentration of chosen product was tested on 3 cupulas. In each multiplate used, three control cupulas containing the globular suspension in RPS 10 medium without the product allowed the maximum rate of proliferation of the culture in 48 hours to be obtained. After an incubation time of 48 hours without renewing the medium in a steam chest with a $CO_2$ content of 5%, the parasitemia content of each cupula was evaluated.

To do this, the canisters were removed from the steam chest and were left for 10 minutes at rest under a hood with laminar flux. The liquid supernatant was removed and a crush preparation was carried out after having homogenized the covering of red blood corpuscles remaining at the bottom of the cupula. On these crush preparations, fixed and colored, the different forms of the parasite were counted for 2000 to 3000 red blood corpuscles per plate. The results were expressed as the percentage of proliferation relative to the controls. The graphical relationship produced between the percentage of parasitemia relative to the controls and the different concentrations of the products used, allowed the $ED_{50}$ (50% Effective Dose) to be calculated.

| Product of Example | FCC2 strain sensitive to chloroquine $ED_{50}$ (μg/ml) | FZ strain resistant to chloroquine $ED_{50}$ (μg/ml) |
|---|---|---|
| 2 | 0.35 | 0.34 |

Various modifications of the compounds and method of the invention may be made without departing from the spirit or scope thereof and it is to be understood that the invention is intended to be limited only as defined in the appended claims.

What we claim is:

1. A compound selected from the group consisting of racemates, enantiomeric and diastereoisomeric forms of a compound of the formula

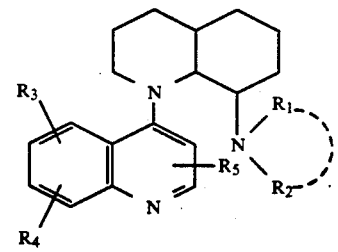

wherein $R_1$ and $R_2$ are individually selected from the group consisting of hydrogen and alkyl of 1 to 5 carbon atoms optionally substituted with at least one halogen, hydroxy, alkyl or alkoxy of 1 to 4 carbon atoms or taken together with the nitrogen to which they are attached form a heterocycle selected from the group consisting of pyrrolidinyl, piperidinyl, morpholinyl, piperazinyl, methylpiperazinyl, ethylpiperazinyl, propylpiperazinyl, phenylpiperazinyl, chlorophenylpiperazinyl, trifluoromethylphenylpiperazinyl and benzylpiperazinyl optionally substituted with at least one member of the group consisting of alkyl or alkoxy of 1 to 5 carbon atoms, benzyl and phenyl, $R_3$ and $R_4$ are individually selected from the group consisting of hydrogen halogen, hydroxy $(C_{1-5})$alkyl and $(C_{1-5})$alkyloxy, both alkyl and alkoxy are optionally substituted with at least one substituent selected from the group consisting of halogen, hydroxy, phenyl, $(C_{1-4})$alkyl and $(C_{1-4})$alkyloxy, $R_5$ is hydrogen or alkyl of 1 to 5 carbon atoms optionally substituted with at least one member of the group consisting of halogen, hydroxy, phenyl, $(C_{1-4})$alkyl and $(C_{1-4})$alkyloxy or a non-toxic, pharmaceutically acceptable acid addition salt or quaternary ammonium salt.

2. A compound of claim 1 wherein $R_1$ and $R_2$ together with the nitrogen form pyrrolidinyl and $R_3$, $R_4$ and $R_5$ individually are selected from the group consisting of hydrogen, halogen and $-CF_3$.

3. A compound of claim 1 selected from the group consisting of (4a α, 8α, 8aα) (±) 1-(7-chloro-4-quinolinyl)-decahydro-8-(1-pyrrolidinyl)-quinoline and (4aα, 8α, 8aα) (±) 1-(7-chloro-4-quinolinyl)-decahydro-8-(1-pyrrolidinyl)-quinoline dihydrochloride.

4. An analgesic composition comprising an analgesically effective amount of at least one compound of claim 1 and an inert pharmaceutical carrier.

5. A composition of claim 4 wherein $R_1$ and $R_2$ together with the nitrogen form pyrrolidinyl and $R_3$, $R_4$ and $R_5$ are individually selected from the group consisting of hydrogen, halogen and $-CF_3$.

6. A composition of claim 4 wherein the active compound is selected from the group consisting of (4aα, 8α, 8a α) (±) 1-(7-chloro-4-quinolinyl)-decahydro-8-(1-pyrrolidinyl)-quinoline and (4a α, 8α, 8aα) (±) 1-(7-chloro-4-quinolinyl)-decahydro-8- (1-pyrrolidinyl)-quinoline dihydrochloride.

7. A method of relieving pain in warm-blooded animals comprising administering to warm-blooded animals an analgesically effective amount of at least one compound of claim 1.

8. A method of claim 7 wherein $R_1$ and $R_2$ together with the nitrogen form pyrrolidinyl and $R_3$, $R_4$ and $R_5$ individually are selected from the group consisting of hydrogen, halogen and $-CH_3$.

9. A method of claim 7 wherein the active compound is selected from the group consisting of (4aα, 8α, 8aα) (±) 1-(7-chloro-4-quinolinyl)-decahydro-8-(1-pyrrolidinyl)-quinoline and (4a α, 8α, 8aα) (±) 1-(7-chloro-4-quinolinyl)-decahydro-8-(1-pyrrolidinyl)-quinoline dihydrochloride.

* * * * *